(12) United States Patent
Yang

(10) Patent No.: US 8,469,509 B2
(45) Date of Patent: Jun. 25, 2013

(54) EYEGLASSES HAVING BILAYERED LENS ASSEMBLY

(75) Inventor: Shun-Tien Yang, Tainan (TW)

(73) Assignee: All-Logic Int. Co., Ltd., Tainan (TW)

( * ) Notice: Subject to any disclaimer, the term of this patent is extended or adjusted under 35 U.S.C. 154(b) by 29 days.

(21) Appl. No.: 13/195,697

(22) Filed: Aug. 1, 2011

(65) Prior Publication Data
US 2012/0236250 A1 Sep. 20, 2012

(30) Foreign Application Priority Data

Mar. 16, 2011 (TW) .............................. 100204675 U

(51) Int. Cl.
*G02C 11/08* (2006.01)
(52) U.S. Cl.
USPC ...................................... 351/62; 2/426; 2/435
(58) Field of Classification Search
USPC ........... 2/426–429, 435–437; 16/228; 351/62, 351/83, 86, 153
See application file for complete search history.

(56) References Cited

U.S. PATENT DOCUMENTS

| 5,018,223 | A | * | 5/1991 | Dawson et al. | 2/436 |
| 5,988,810 | A | * | 11/1999 | Geyer | 351/110 |
| 6,009,564 | A | * | 1/2000 | Tackles et al. | 2/436 |
| 6,959,988 | B1 | * | 11/2005 | Sheldon | 351/106 |
| 7,543,929 | B2 | * | 6/2009 | Yang | 351/62 |
| 8,083,344 | B2 | * | 12/2011 | Blanshay et al. | 351/62 |

OTHER PUBLICATIONS

US 2009/188023 A1, Hsu, Roger Wei Yi, Air Vent Eyeglasses Construction, Jul. 30, 2009.*

* cited by examiner

*Primary Examiner* — Jordan Schwartz
*Assistant Examiner* — William Alexander
(74) *Attorney, Agent, or Firm* — Marger, Johnson & McCollom, P.C.

(57) ABSTRACT

A pair of eyeglasses includes a first frame, a front lens unit, a rear lens unit, a spacer frame unit for spacing the front and rear lens units, and a second frame mounted behind the first frame. The first frame includes a first frame section and a second frame section extending rearwardly from the first frame section and having a plurality of lens-engaging holes. The front lens unit includes a plurality of retaining blocks inserted respectively into the lens-engaging holes. The spacer frame unit is aligned with the first frame section in a front-to-rear direction, and includes at least one spacer frame having an inner periphery not projecting inwardly from an inner periphery of the first frame section.

16 Claims, 7 Drawing Sheets

EYEGLASSES HAVING BILAYERED LENS ASSEMBLY

CROSS-REFERENCE TO RELATED APPLICATION

This application claims priority of Taiwanese Application No. 100204675, filed on Mar. 16, 2011.

BACKGROUND OF THE INVENTION

1. Field of the Invention

This invention relates to eyeglasses, and more particularly to eyeglasses having a bilayered lens assembly.

2. Description of the Related Art

Referring to FIGS. 1 and 2, a conventional fog-free goggle 1 includes a frame 11, a front lens 12 mounted on the frame 11, a rear lens 13 spaced apart from and disposed behind the front lens 12, and a spacer frame 14 disposed between the front and rear lenses 12, 13 for spacing the front and rear lenses 12, 13. The front lens 12 has a plurality of mounting grooves 121 formed along a periphery thereof. The frame 11 has a plurality of retaining blocks 111 inserted respectively into the mounting grooves 121. As such, since a sealed space is defined between the front and rear lenses 12, 13, formation of fog in the goggle 1 can be prevented when the goggle 1 is worn on a wearer and comes into contact with cold air.

However, since the spacer frame 14 projects inwardly from an inner periphery of the frame 11, the visual field (A) of the wearer becomes relatively small.

To maintain the visual field (A) at normal size, it is necessary to increase the height and width of the goggle. As a result, the total size and weight of the goggle get larger, which does not meet the need of consumers.

SUMMARY OF THE INVENTION

The object of this invention is to provide fog-free eyeglasses that allow the wearer to have a sufficient large visual field and that have a sufficient small size.

Accordingly, a pair of eyeglasses of this invention includes a first frame, a front lens unit, a rear lens unit, a spacer frame unit for spacing the front and rear lens units, and a second frame mounted behind the first frame. The first frame includes a first frame section and a second frame section extending rearwardly from the first frame section and having a plurality of lens-engaging holes. The front lens unit includes a plurality of retaining blocks inserted respectively into the lens-engaging holes. The spacer frame unit is aligned with the first frame section in a front-to-rear direction, and includes at least one spacer frame having an inner periphery not projecting inwardly from an inner periphery of the first frame section.

Since the inner periphery of the spacer frame does not project inwardly from the inner periphery of the first frame section, occurrence of the spacer frame cannot result in a reduction in the visual field of a person wearing the eyeglasses.

BRIEF DESCRIPTION OF THE DRAWINGS

These and other features and advantages of this invention will become apparent in the following detailed description of a preferred embodiment of this invention, with reference to the accompanying drawings, in which.

DETAILED DESCRIPTION OF THE PREFERRED EMBODIMENT

Figure 1:
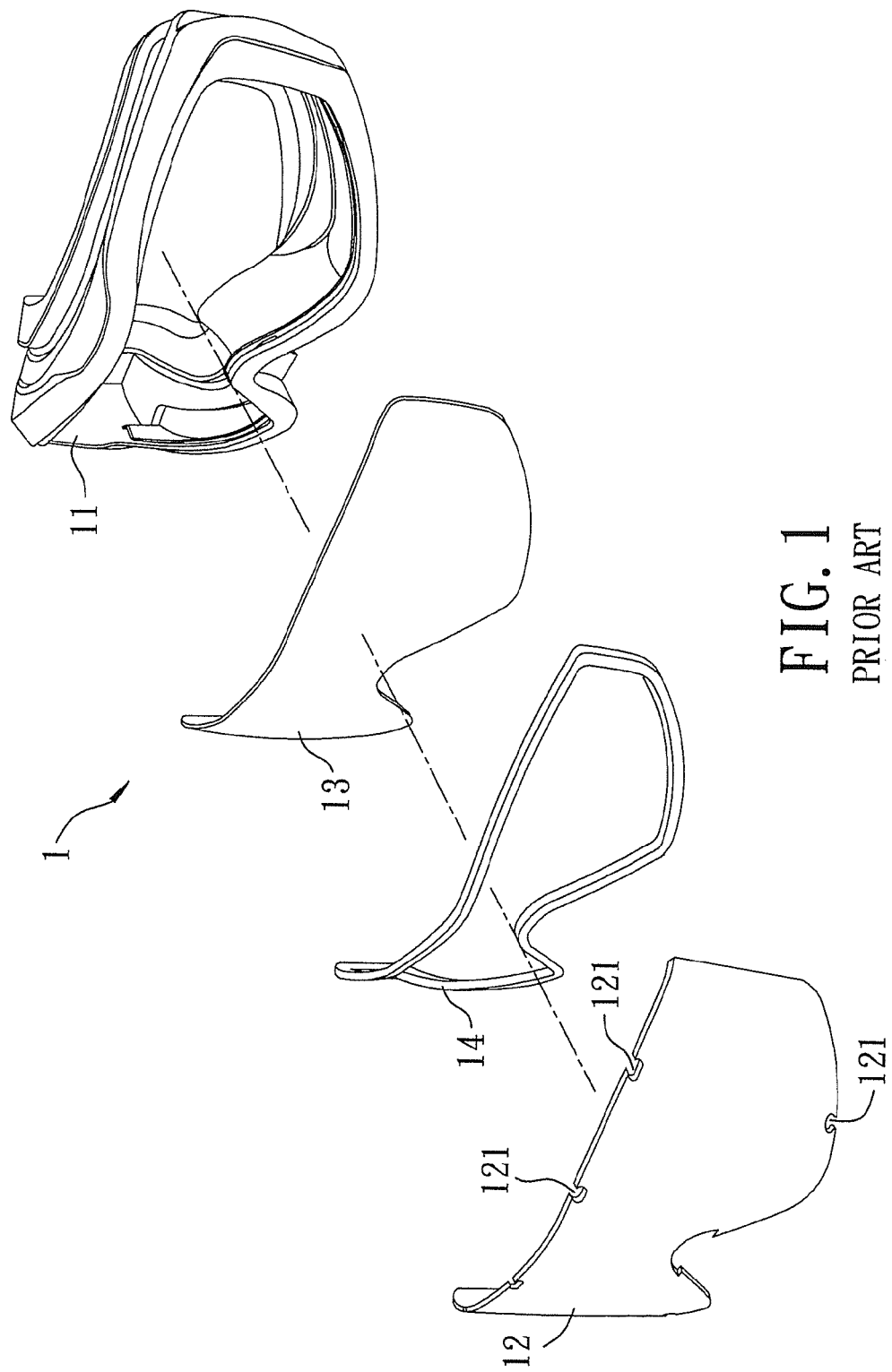
FIG. 1 is an exploded perspective view of a conventional fog-free goggle.
Figure 2:
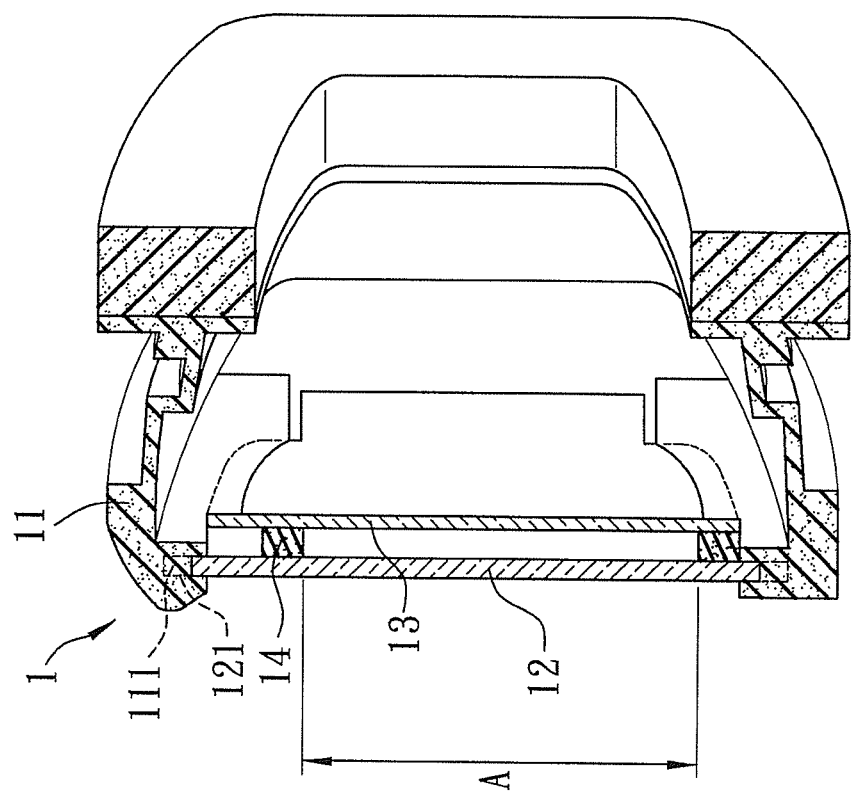
FIG. 2 is a sectional view of the conventional fog-free goggle.
Figure 3:
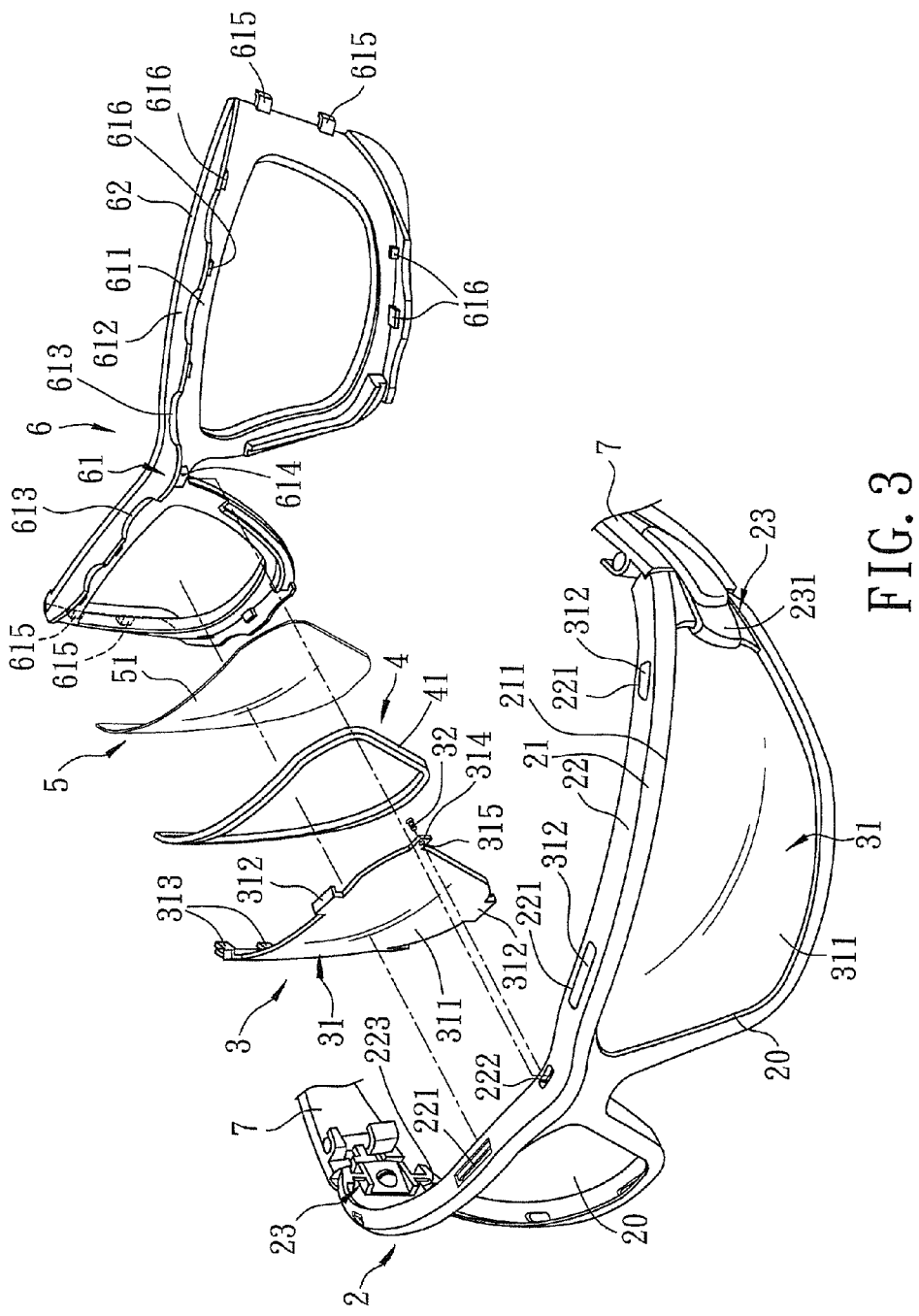
FIG. 3 is a fragmentary, partly exploded perspective view of the preferred embodiment of fog-free eyeglasses according to this invention.
Figure 4:
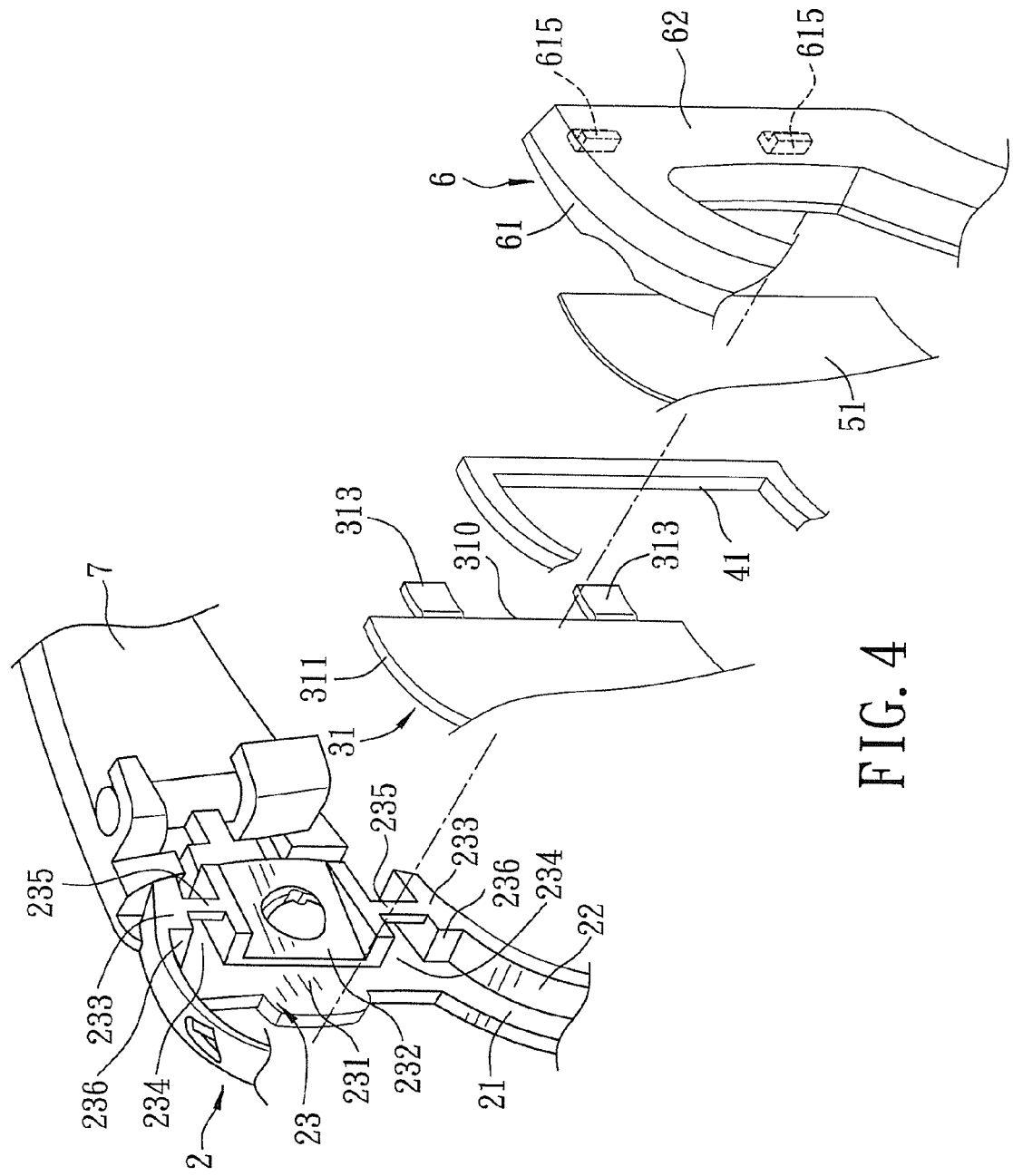
FIG. 4 is a fragmentary, partly exploded perspective view of the preferred embodiment, illustrating a mounting section of a first frame.
Figure 5:
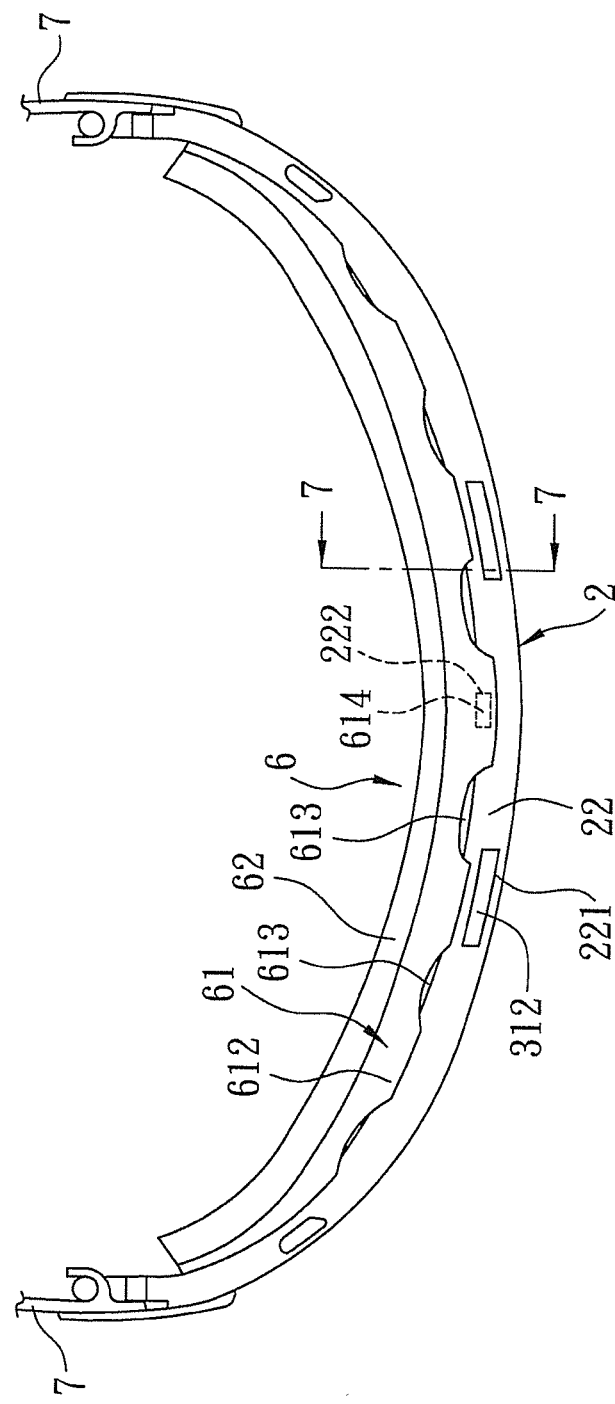
FIG. 5 is a fragmentary top view of the preferred embodiment.

Referring to FIGS. 3, 4, and 5, the preferred embodiment of fog-free eyeglasses according to this invention includes a first frame 2, a front lens unit 3, a spacer frame unit 4, a rear lens unit 5, a second frame 6, and two temples 7 assembled to the first frame 2. The fog-free eyeglasses may be industrial safety glasses, snow glasses, etc.

The first frame 2 defines two lens-mounting spaces 20 spaced apart from each other in a left-to-right direction, and includes a first frame section 21 surrounding the mounting spaces 20, a second frame section 22 extending rearwardly from an outer periphery of the first frame section 21, and two mounting sections 23 connected respectively to left and right sides of each of the first and second frame sections 21, 22 and permitting the temples 7 to be mounted respectively thereon. The second frame section 22 has a plurality of lens-engaging holes 221 each formed therethrough in an upright direction and in spatial communication with the corresponding lens-mounting space 20, and a first mounting hole 222 formed in a middle of a top portion thereof.

Each of the mounting sections 23 includes a front wall 231, a generally U-shaped middle wall 232 extending rearwardly from a central portion of the front wall 231, a pair of top and bottom walls 233 extending rearwardly from the front wall 231 and disposed respectively above and below the middle wall 232, two second mounting holes 234 each defined between the middle wall 232 and a respective one of the top and bottom walls 233, and two bridging walls 235 each connected between the middle wall 232 and a respective one of the top and bottom walls 233. Each of the top and bottom walls 233 has a stop surface 236 facing the lens-mounting spaces 20.

The front lens unit 3 includes two front lenses 31 mounted respectively within the lens-mounting spaces 20, and two lock bolts 32 (only one is shown in FIG. 3) for locking the front lenses 31 on the first frame 2. Each of the front lenses 31 includes a lens body 311 having a lateral side 310 adjacent to the corresponding mounting section 23, a plurality of retaining blocks 312 extending from the lens body 311, two side connecting blocks 313 extending from the lateral side 310 and inserted respectively into the second mounting holes 234 in the corresponding mounting section 23 of the first frame 2, and a lock block 314 extending from the lens body 311 toward the other one of the front lenses 31 and having a hole 315 formed therethrough. The retaining blocks 313 of the front lenses 31 are inserted respectively into the lens-engaging holes 221 in the first frame 2.

Figure 6:
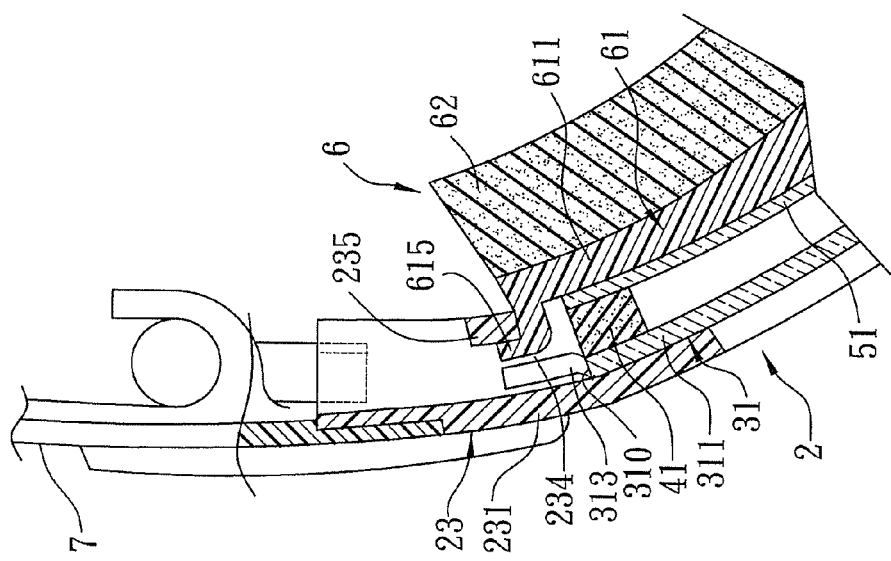
FIG. 6 is a fragmentary sectional view of the preferred embodiment.

With particular reference to FIGS. 3, 4, and 6, the lateral sides 310 of the front lenses 31 abut respectively against the stop surfaces 236 of the mounting sections 23 of the first frame 2. Each of the lock bolts 32 extends through the hole 315 in the lock block 314 of the corresponding front lens 31, and is threaded to the first frame 2 for locking the corresponding front lens 31 on the first frame 2.

Figure 7:
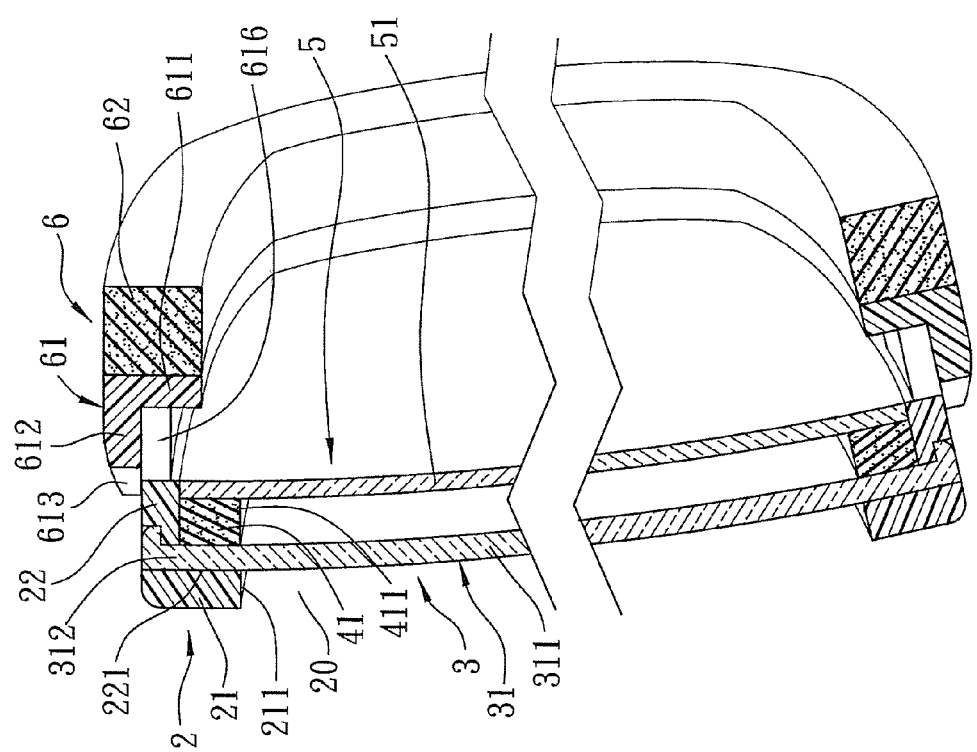
FIG. 7 is a sectional view taken along line 7-7 in FIG. 5.

With particular reference to FIGS. 3 and 7, the spacer frame unit 4 includes two spacer frames 41 attached respectively and fixedly to the front lenses 31 and extending respectively along outer peripheries of the lens bodies 311 of the front lenses 31. Outer peripheries of the spacer frames 41 abut against the second frame section 22 of the first frame 2. The spacer frames 41 are aligned with and spaced apart from the first frame section 21 of the first frame 2 in a front-to-rear direction.

The rear lens unit 5 includes two rear lenses 51 arranged in the left-to-right direction and attached respectively and fixedly to and disposed behind the spacer frames 41. The rear lenses 51 are aligned respectively with and spaced apart from the front lenses 31 in the front-to-rear direction.

The spacer frame unit 4 cooperates with the front and rear lens units 3, 5 to constitute a bilayered lens assembly.

The second frame 6 is attached fixedly to and disposed behind the first frame 2, and includes a rigid frame portion 61 disposed at a front side thereof, and a soft frame portion 62 attached fixedly to and disposed behind the rigid frame portion 61. The soft frame portion 62 is adapted for contact with a face of a user, thereby providing a comfort feeding to the user. The rigid frame portion 61 has a surrounding section 611 attached fixedly to the soft frame portion 62, and a retaining section 612 extending forwardly from the surrounding frame section 611 and connected to the first frame 2. The retaining section 612 is disposed around the rear lens unit 5, and has a plurality of vent holes 613, each of which is concaved rearwardly and is formed therethrough in the upright direction.

With particular reference to FIGS. 3, 4, 6, and 7, the rigid frame portion 61 further has a first mounting block 614 extending downwardly from a middle of a top portion thereof, four second mounting blocks 615 extending from the surrounding frame section 611, and a plurality of projecting blocks 616 extending forwardly from the surrounding frame section 611. The first mounting block 614 is inserted into the first mounting hole 222 in the first frame 2. The second mounting blocks 615 are inserted respectively into the second mounting holes 234 in the first frame 2. As such, the second frame 6 is attached fixedly to the first frame 2. Each of the second mounting blocks 615 is confined among the middle wall 232, a corresponding one of the top and bottom walls 233, and the corresponding bridging wall 235 of the corresponding mounting section 23 of the first frame 2.

It should be noted that, the number of the second mounting blocks 615 may be reduced to two. If this occurs, the number of the second mounting holes 234 needs to be also reduced to two. In this state, the same effect of positioning the second frame 6 relative to the first frame 2 can be achieved.

Since the spacer frames 41 are aligned with the first frame section 21 of the first frame 2, as described above, inner peripheries 411 (see FIG. 7) of the spacer frames 41 do not project inwardly from inner peripheries 211 of the first frame section 21 of the first frame 2 defining respectively defining the lens-mounting spaces 20, thereby minimizing adverse affection of the spacer frames 41 with respect to the visual field of the wearer.

Furthermore, with particular reference to FIGS. 3, 5, and 7, due to inclusion of the vent holes 613 in the second frame 6, heat and moisture can be dissipated from the face of the wearer therethrough, so as to prevent formation of fog in the eyeglasses. Furthermore, the projecting blocks 616 space the surrounding frame section 611 of the second frame 6 and the second frame section 22 of the first frame 2, so as to facilitate dissipation of heat and moisture from the face of the user through the vent holes 613.

Alternatively, each of the front and rear lens units 3, 5 may include only one lens 31, 51 in the same manner as the above-mentioned prior art. In case of the single-lens front and rear lens units, the first and second frames 2, 6 must be modified correspondingly, and only one spacer frame 41 is required.

In view of the above, the fog-free eyeglasses of this invention allow the wearer to have a sufficient large visual field without increasing the total size of the eyeglasses. Thus, the object of this invention is achieved.

With this invention thus explained, it is apparent that numerous modifications and variations can be made without departing from the scope and spirit of this invention. It is therefore intended that this invention be limited only as indicated by the appended claims.

I claim:

1. Eyeglasses comprising:
   a first frame including a first frame section;
   a front lens unit including at least one front lens disposed removably within said first frame;
   a spacer frame unit including at least one spacer frame aligned with said first frame and attached fixedly to and disposed behind said front lens;
   a rear lens unit attached fixedly to and disposed behind said spacer frame and spaced apart from said front lens unit in a front-to-rear direction; and
   a second frame attached fixedly to and disposed behind said first frame;
   wherein said first frame defines two lens-mounting spaces spaced apart from each other in a left-to-right direction, said front lens unit including two said front lenses disposed respectively within said lens-mounting spaces in said first frame, said rear lens unit including two rear lenses aligned respectively with said front lenses and attached fixedly to and disposed behind said spacer frame;
   wherein said spacer frame unit includes two said spacer frames attached respectively and fixedly to and disposed behind said front lenses, each of said spacer frames extending along an outer periphery of said lens body of a corresponding one of said front lenses.

2. The eyeglasses as claimed in claim 1, wherein said second frame includes a rigid frame portion mounted to said first frame, and a soft frame portion attached fixedly to said rigid frame portion.

3. The eyeglasses as claimed in claim 2, wherein said rigid frame portion has a surrounding frame section attached fixedly to said soft frame portion, and a retaining section extending forwardly from said surrounding frame section and connected to said first frame, said retaining section being disposed around said rear lens unit and having a plurality of vent holes defined by said first frame and said retaining section of said second frame.

4. The eyeglasses as claimed in claim 3, wherein said rigid frame portion further has a plurality of projecting blocks extending from said surrounding frame section and abutting against said second frame section of said first frame for spacing said surrounding frame section and said second frame section.

5. The eyeglasses as claimed in claim 2, wherein said first frame section of said first frame has an outer periphery, said first frame further including a second frame section extending rearwardly from said outer periphery of said first frame section and having a plurality of lens-engaging holes each formed therethrough in an upright direction and including a lens body and a plurality of retaining blocks extending from said lens body and inserted respectively into said lens-engaging holes in said first frame, said second frame section of said first frame further having a top portion formed with a first mounting hole, said first frame further including two mounting sections, each of which is connected to a corresponding one of left and right sides of each of said first and second frame sections and is formed with a second mounting hole, said rigid frame section of said second frame having a surrounding frame section attached fixedly to said soft frame portion, a retaining section extending forwardly from said surrounding frame section, a first mounting block extending downwardly from a top portion of said retaining section and inserted into said first mounting hole in said first frame, and two second mounting blocks extending respectively from left and right sides of said surrounding frame section of said rigid frame portion of said second frame and inserted respectively into said second mounting holes in said first frame.

6. The eyeglasses as claimed in claim 2, wherein said second frame section of said first frame further has a first mounting hole formed in a top portion thereof, said first frame further including two mounting sections connected respectively to left and right sides of each of said first and second frame sections, each of said mounting sections including a front wall, a middle wall extending rearwardly from said front wall, a pair of top and bottom walls extending rearwardly from said front wall and disposed respectively above and below said middle wall, two second mounting holes each defined between said middle wall and a respective one of said top and bottom walls, and two bridging walls each connected between said middle wall and a respective one of said top and bottom walls, said rigid frame portion of said second frame having a surrounding frame section attached fixedly to said soft frame portion, a retaining section extending forwardly from said surrounding frame section and connected to said first frame, a first mounting block extending downwardly from a top portion of said retaining section, and four second mounting blocks extending from said surrounding frame section and inserted respectively into said second mounting holes in said first frame.

7. The eyeglasses as claimed in claim 6, wherein said front lens unit includes two said front lenses, said lens body of each of said front lenses having a lateral side adjacent to a corresponding one of said mounting sections of said first frame, each of said front lenses further including two side connecting blocks extending from said lateral side and inserted respectively into said second mounting holes in a corresponding one of said mounting sections of said first frame.

8. The eyeglasses as claimed in claim 7, wherein each of said front lenses further includes a lock block extending from said lens body toward the other one of said front lenses and having a hole formed therethrough, said front lens unit further including two lock bolts extending respectively through said holes in said lock bolts of said front lenses and threaded to said first frame for locking said front lenses on said first frame.

9. A double lens pair of eyeglasses, comprising:
a first frame with a front lens unit and a rear lens unit,
the front lens unit comprising a front lens mounted therein and the rear lens unit comprising a rear lens mounted therein,
a spacer frame unit for spacing apart the front and rear lens units,
a second frame attached to the first frame such that at least one vent hole is formed by an outside edge of the first frame and by an outside edge of the second frame.

10. The double lens pair of eyeglasses of claim 9, wherein a plurality of vent holes are formed around the periphery of the attached first and second frames.

11. The double lens pair of eyeglasses of claim 9, wherein a plurality of concaved shaped vent holes are formed in the upright direction.

12. The double lens pair of eyeglasses of claim 9, wherein the rear lenses are aligned with and spaced apart from the front lenses in the front-to-rear direction.

13. The double lens pair of eyeglasses as defined in claim 9, wherein the second frame is removably attached to the first frame.

14. A pair of eyeglasses, comprising:
a first frame with at least one lens unit for mounting a lens,
a second frame comprising a rigid frame portion and a soft frame portion with the rigid frame portion fixedly attached to the soft frame portion,
the rigid frame portion connecting to the first frame such that at least one vent hole is formed in an open space formed by both the rigid frame portion and the first frame.

15. The eyeglasses as defined in claim 14 wherein a plurality of vent holes are formed around the periphery of the connected frame portions.

16. The eyeglasses as defined in claim 14 wherein the soft frame portion comprises a soft material that is mountable to the face of a wearer.

* * * * *